(12) United States Patent
Takabatake et al.

(10) Patent No.: US 7,968,713 B2
(45) Date of Patent: Jun. 28, 2011

(54) METHOD OF SYNTHESIZING QUINOXALINE DERIVATIVE BY MICROWAVE IRRADIATION

(75) Inventors: Toru Takabatake, Tokyo (JP); Hiroaki Saito, Tokyo (JP); Yusuke Sumiyoshi, Tokyo (JP)

(73) Assignee: Nihon University, Tokyo (JP)

( * ) Notice: Subject to any disclaimer, the term of this patent is extended or adjusted under 35 U.S.C. 154(b) by 117 days.

(21) Appl. No.: 11/991,799

(22) PCT Filed: Oct. 16, 2006

(86) PCT No.: PCT/JP2006/320560
§ 371 (c)(1),
(2), (4) Date: Mar. 11, 2008

(87) PCT Pub. No.: WO2007/043680
PCT Pub. Date: Apr. 19, 2007

(65) Prior Publication Data
US 2009/0048445 A1 Feb. 19, 2009

(30) Foreign Application Priority Data
Oct. 14, 2005 (JP) ................................ 2005-300444

(51) Int. Cl.
*C07D 241/36* (2006.01)
(52) U.S. Cl. ........................................................ 544/355
(58) Field of Classification Search ................... 544/355
See application file for complete search history.

(56) References Cited

U.S. PATENT DOCUMENTS
4,343,942 A 8/1982 Issidorides et al.
2004/0242684 A1 12/2004 Chen et al.

FOREIGN PATENT DOCUMENTS
GB 2297089 * 7/1996
WO WO 95/24190 * 9/1995

OTHER PUBLICATIONS

Haddadin, et al. JOC, 36(4), 1971, 514-518.*
Haddadin, et al. Tetrahedron, 32(6), 1976, 719-724.*
Tohru Takabatake, et al., "Synthesis and Antibacterial Properties of Quinoxaline 1,4-Dioxide Derivatives," Yakugaku Zasshi, vol. 116 (6), p. 491-496, 1996.
Hala U. Gali-Muhtasib,et al., "Quinoxaline 1,4-dioxides as anticancer and hypoxia-selective drugs," Oncology Reports vol. 8, p. 679-684, 2001.
Antonio Monge, et al., "Hypoxia-Selective Agents Derived from Quinoxaline 1,4-Di-N-oxides," J. Med. Chem. vol. 38, p. 1786-1792, 1995.
Adil A. Jarrar, et al., "Photolysis of Some Quinoxaline-1,4-dioxides. A Method of Structural Assignment," Heterocycles, vol. 4, No. 6, p. 1077-1082, 1976.
Costas H. Issidorides, et al., "Benzofurazan Oxide. II. Reactions with Enolate Anions," Journal of Organic Chemistry, vol. 31, p. 4067-4068, 1966.
Tohru Takabatake, et al., "The Reactions of Benzofuroxan with Carbonyl Compounds on the Surface of Solid Catalysts," Journal of Heterocyclic Chemistry, vol. 30 (6), p. 1477-1479, 1993.
Nobuo Sekimura, et al., "Synthesis of quinoxaline 1,4-dioxides from 5,6-diethylbenzofuroxan on silica gel," Heterocycles, vol. 65, No. 7, p. 1589-1600, 2005.
Hideko Koshima, "Use of Microwaves in Organic Synthesis," Kagaku Kougyou, p. 58-63, 2002.
Masao Tokuda, "Environmentally Benign Organic Synthesis," Kagaku Kougyou, p. 21-25, 2002.
Andres Jaso, et al, "Synthesis of new 2-acetyl and 2-benzoyl quinoxaline 1,4-di-N-oxide derivatives as anti-*Mycobacterium tuberculosis* agents," European Journal of Medicinal Chemistry, vol. 38 (9), p. 791-800, 2003.

* cited by examiner

*Primary Examiner* — James O Wilson
*Assistant Examiner* — Douglas M Willis
(74) *Attorney, Agent, or Firm* — Morgan, Lewis & Bockius LLP

(57) ABSTRACT

There is disclosed a method of synthesizing a quinoxaline derivative in which toxicity, corrosiveness and permeation are low and which is excellent in safety and which attains a reduced reaction time, a greatly improved yield and excellent economical efficiency. The object is achieved by a method of synthesizing a quinoxaline derivative which comprises adsorbing a benzofuroxan derivative and a β-diketone derivative on a solid support, and then heating the derivatives in a solid state by microwave irradiation to dehydrocyclize them. An example of a quinoxaline derivative is a compound of formula (4):

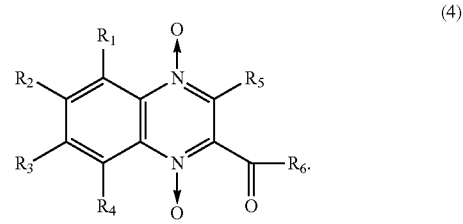

(4)

1 Claim, No Drawings

METHOD OF SYNTHESIZING QUINOXALINE DERIVATIVE BY MICROWAVE IRRADIATION

TECHNICAL FIELD

The present invention relates to a method of synthesizing a quinoxaline derivative by microwave irradiation heating, and a novel quinoxaline 1,4-dioxide derivative. More particularly, it relates to a method of synthesizing a quinoxaline derivative in which toxicity, corrosiveness and permeation are low and which is excellent in safety and which attains a reduced reaction time, a greatly improved yield and excellent economical efficiency, and it also relates to a novel quinoxaline 1,4-dioxide derivative.

BACKGROUND ART

It is known that a quinoxaline derivative has an antibacterial property (Non-Patent Document 1) and hypoxic cytotoxicity (Non-Patent Document 2).

Moreover, it is reported that a quinoxaline 1,4-dioxide derivative selectively develops toxicity in a hypoxic cell (Non-Patent Document 3). The quinoxaline 1,4-dioxide derivative is subjected to in vivo reduction in a hypoxic state, and converted into a radical compound having high reactivity (disturbance in the cell), and the resultant radicals exert especially strong cytotoxicity in the hypoxic state. Many cancers are solid cancers, capillary vessels of solid cancer tissues are destroyed owing to abnormal cell proliferation, hence the tissues are isolated from other tissues, and neogenesis of blood vessels cannot catch up with the cell proliferation, so that oxygen and nutrition are not sufficiently supplied to the tissues, thereby bringing the tissues into the hypoxic state. Therefore, it can be expected that the present quinoxaline 1,4-dioxide derivative does not much disturb normal tissues to which oxygen is sufficiently supplied, and peculiarly disturbs a seat of disease only.

Heretofore, the quinoxaline derivative is synthesized by Beirut reaction in which a β-diketone compound is added to benzofuroxan in the presence of a basic catalyst such as triethylamine, and then dehydrocyclized. For example, it is reported that to synthesize 2-benzoyl-6,7-dichloro-3-phenylquinoxaline 1,4-dioxide owing to Beirut reaction, a reaction time is 24 hours, and a yield is 36% (Non-Patent Documents 4, 5).

Non-Patent Document 1: Journal of the Pharmaceutical Society of Japan, Vol. 116, No. 6, 491 to 496
Non-Patent Document 2: Oncology Reports 8, 679 to 684 (2001)
Non-Patent Document 3: J. Med. Chem. 1995, 38, 1786 to 1792
Non-Patent Document 4: Heterocycles Vol. 4, No. 6, 1077 to 1082 (1976)
Non-Patent Document 5: Journal of Organic Chemistry Vol. 31, 4067 to 4068 (1966)

DISCLOSURE OF THE INVENTION

Problem to be Solved by the Invention

However, Beirut reaction is a one-pot reaction and a simple synthesis process, but is a liquid phase reaction performed by use of a basic catalyst by a heating process in an oil bath or the like, and hence the reaction has the following respects to be improved.

First, a flammable solvent is used during heating, so that safety is low. That is, many of the basic catalysts for use have corrosiveness, when they come in contact with skin. A basic catalyst such as triethylamine is a substance which is a liquid at ordinary temperature, and has large permeation with respect to the skin. Even when a solid basic catalyst is used, a system causes the liquid phase reaction, so that during the reaction, when the catalyst is attached to the skin, the catalyst has large permeation and low safety.

Moreover, the Beirut reaction is performed on a condition of a base, it is therefore difficult to synthesize a derivative having a functional group with an unstable base, and a yield of a target cannot sufficiently be secured in many cases.

Furthermore, a reaction time of the Beirut reaction requires a comparatively long time of an hour unit or a day unit. During the heating process in the oil bath or the like, reaction heat is transmitted to a reactant owing to heat conduction and convection, the reaction proceeds, much energy is consumed, and improvement of economical efficiency is demanded.

In addition, to regenerate a catalyst base, an operation such as distilling is laborious. To discard the catalyst base, an operation such as a neutralization treatment is also laborious.

To solve the problem, an object of the present invention is to provide a method of synthesizing a quinoxaline derivative in which toxicity, corrosiveness and permeation are low and which is excellent in safety and which attains a reduced reaction time, a greatly improved yield and excellent economical efficiency.

Another object of the present invention is to provide a novel quinoxaline 1,4-dioxide derivative.

Means for Solving the Problem

As a result of intensive investigations, the present inventors have found an excellent quinoxaline derivative synthesizing method characterized by comprising adsorbing a benzofuroxan derivative and a β-diketone derivative on a solid support, and then heating the derivatives in a solid state by microwave irradiation to dehydrocyclize them, the inventors also have found a novel quinoxaline 1,4-dioxide derivative, and they have completed the present invention.

That is, according to the present invention, there are provided: [1] a method of synthesizing a quinoxaline derivative, characterized by comprising adsorbing a benzofuroxan derivative and a β-diketone derivative on a solid support, and then heating the derivatives in a solid state by microwave irradiation to dehydrocyclize them; [2] a method of synthesizing a quinoxaline derivative, characterized by comprising adsorbing a benzofuroxan derivative represented by general formula (1) and a β-diketone derivative represented by general formula (2) on a solid support, and then heating the derivatives in a solid state by microwave irradiation to dehydrocyclize them; [3] the method of synthesizing the quinoxaline derivative according to the above [2], wherein the quinoxaline derivative is a quinoxaline 1,4-dioxide derivative represented by general formula (3); [4] the method of synthesizing the quinoxaline derivative according to the above [2], wherein the quinoxaline derivative is a quinoxaline 1,4-dioxide derivative represented by general formula (4); [5] the method of synthesizing the quinoxaline derivative according to any one of the above [1] to [4], wherein the solid support is silica gel, alumina or a molecular sieve; and [6] a quinoxaline 1,4-dioxide derivative which is represented by general formula (4).

A reaction step in the method of synthesizing the quinoxaline derivative according to the present invention is as follows:

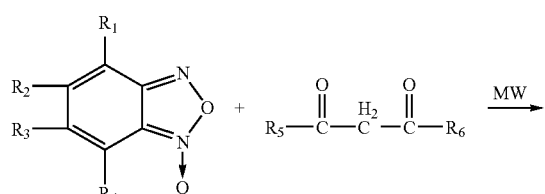

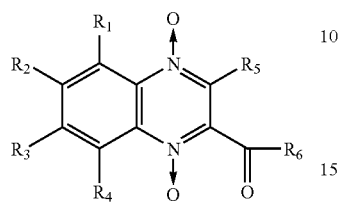

EFFECT OF THE INVENTION

In a method of synthesizing a quinoxaline derivative according to the present invention, a base is not used as a catalyst, and a solid support is used, so that there is provided a method of synthesizing a quinoxaline derivative in which toxicity, corrosiveness and permeation are low and which is excellent in safety and which attains a reduced reaction time, a greatly improved yield and excellent economical efficiency, and there is further provided a novel quinoxaline 1,4-dioxide derivative.

BEST MODE FOR CARRYING OUT THE INVENTION

A method of synthesizing a quinoxaline derivative according to the present invention is characterized in that a benzofuroxan derivative and a β-diketone derivative are adsorbed on a solid support, then heated in a solid state by microwave irradiation, and dehydrocyclized.

In the present invention, the heating is performed in the solid state by the microwave irradiation to perform the dehydrocyclization, so that molecules of an organic compound having an electric dipole vibrate in an intense electric field made by vibrating microwaves, frictional heat is generated among the molecules to change to heat, a temperature of a molecular level rapidly rises, and reaction proceeds. Thus, as compared with a heating process in an oil bath or the like due to heat conduction and convection, the microwave irradiation heating is not a method in which reaction heat is transmitted to a reactant owing to the heat conduction and convection, but is a method for directly heating the molecules by the microwave irradiation, so that the heating of the molecular level occurs, and as compared with a conventional method, the present method does not have any loss in energy and is economically efficient.

Moreover, Beirut reaction (the conventional method) in which a basic catalyst is used requires a reaction time of 24 hours, whereas in the present invention, the reaction time is only about several minutes which is 1/60 to 1/720 of the reaction time of the conventional method, and the present method is very economically efficient.

Furthermore, a yield of the conventional method is 36%, whereas in the present invention, a yield of a novel substance is 36 to 90%, and a yield of a known substance remarkably improves as much as about 2.5 times a conventional yield.

In addition, according to the present invention, the heating reaction is performed in a solid phase. As compared with a liquid phase reaction in which a flammable solvent is used, any fire is not caught, and safety is high.

In the method of synthesizing the quinoxaline derivative according to the present invention, preferably a benzofuroxan derivative represented by the following general formula (1) and a β-diketone derivative represented by the following general formula (2) are adsorbed on a solid support, then heated in a solid state by microwave irradiation, and dehydrocyclized.

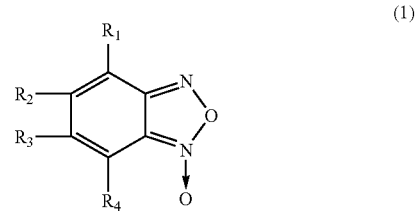

in which $R_1$ is hydrogen or a $C_1$ to $C_4$ alkyl group, $R_2$ and $R_3$ are each hydrogen, a $C_1$ to $C_4$ alkyl group or a halogen atom, and $R_4$ is hydrogen or a $C_1$ to $C_4$ alkyl group.

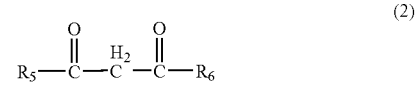

in which $R_5$ is a $C_1$ to $C_4$ alkyl group, a methoxy group or an aryl group, and $R_6$ is a $C_1$ to $C_4$ alkyl group, a methoxy group, an ethoxy group, an aryl group or one of the following groups:

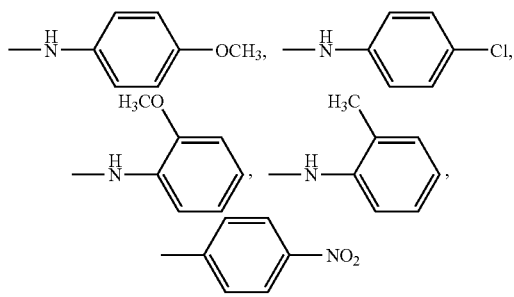

In the method of synthesizing the quinoxaline derivative according to the present invention, the quinoxaline derivative is preferably a quinoxaline 1,4-dioxide derivative represented by the following general formula (3).

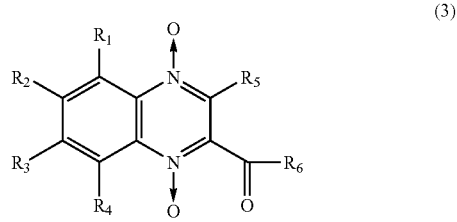

in which $R_1$ is hydrogen or a $C_1$ to $C_4$ alkyl group, $R_2$ and $R_3$ are each hydrogen, a $C_1$ to $C_4$ alkyl group or a halogen atom, $R_4$ is hydrogen or a $C_1$ to $C_4$ alkyl group, $R_5$ is a $C_1$ to $C_4$ alkyl group, a methoxy group or an aryl group, and $R_6$ is a $C_1$ to $C_4$ alkyl group, a methoxy group, an ethoxy group, an aryl group or one of the following groups:

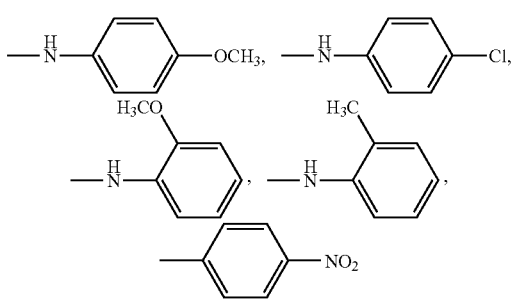

In the above general formulas (1) and (3), $R_1$ is preferably hydrogen, a methyl group or an ethyl group, $R_2$ and $R_3$ are each preferably hydrogen, a methyl group, an ethyl group or a chlorine atom, and $R_4$ is preferably hydrogen, a methyl group or an ethyl group.

In the above general formulas (1) and (3), when both of $R_1$ and $R_4$ are especially preferably hydrogen, a high yield is obtained. When $R_2$ and $R_3$ are the same group, the high yield is obtained. When one of $R_2$ and $R_3$ is hydrogen, two quinoxaline derivatives are obtained from a reaction mechanism, and a combined yield of the two derivatives is high.

In the above general formulas (2) and (3), $R_5$ is preferably a methyl group, a methoxy group or a phenyl group, and $R_6$ is preferably a methyl group, a methoxy group, an ethoxy group or a phenyl group.

Alternatively, in the method of synthesizing the quinoxaline derivative according to the present invention, it is preferable that the quinoxaline derivative is a quinoxaline 1,4-dioxide derivative represented by the following general formula (4).

(4)

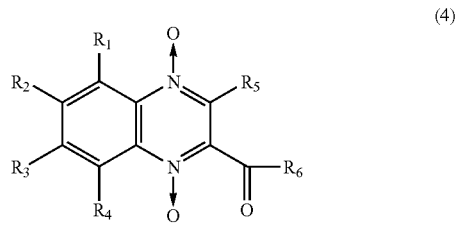

in which $R_1$ is hydrogen,
$R_2$ and $R_3$ are each hydrogen, a halogen atom or a methoxy group,
$R_4$ is hydrogen,
$R_5$ is a $C_1$ to $C_4$ alkyl group or an aryl group, and
$R_6$ is a $C_1$ to $C_4$ alkyl group, an aryl group or the following.

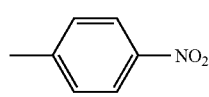

In the method of synthesizing the quinoxaline derivative according to the present invention, it is preferable that the solid support is silica gel, alumina or a molecular sieve. More preferably, silica gel is used. Silica gel is a weak solid acid, has only low toxicity, does not have any corrosiveness against skin, and hardly has permeation. In the method of synthesizing the quinoxaline derivative according to the present invention, a dehydrating function of silica gel or the like is utilized, so that when the reaction ends and then silica gel or the like is heated and dried, the support is easily regenerated, and this is economically efficient.

As an especially preferable support, commercially available column chromatography silica gel for separation and purification is used. In a case where the commercially available column chromatography silica gel for separation and purification is used, silica gel which has adsorbed quinoxaline produced by the reaction may be purified by column chromatography, so that a purifying operation after the reaction is facilitated.

Alternatively, according to the present invention, there is provided a quinoxaline 1,4-dioxide derivative which is represented by the above general formula (4).

In the above general formula (4), $R_2$ and $R_3$ are each preferably hydrogen, a fluoro group, a chloro group or a methoxy group, $R_5$ is preferably a methyl or phenyl group, and $R_6$ is preferably a methyl group, a phenyl group or the following:

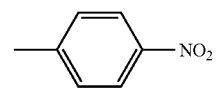

EXAMPLES

The present invention will hereinafter be described in more detail in accordance with examples, but the present invention is not limited to these examples. Any person skilled in the art can variously modify and carry out the present invention in addition to the following examples, and such modification is also included in the scope of the present invention.

Example 1

Synthesis of 2-benzoyl-6,7-dichloro-3-phenylquinoxaline 1,4-dioxide 5,6-dichlorobenzofuroxan (41 mg, 0.2 mmol) and dibenzoylmethane (47.1 mg, 1.05 eqs) were dissolved in 8 mL of dichloromethane, and 6 g of silica gel (wakogel C-200) was then added thereto, followed by evaporating a solvent, to adsorb them on the silica gel. Afterward, the solvent was completely removed with a vacuum pump, and the material was irradiated with microwaves (700 W) for two minutes. The resultant reaction product was extracted with ethyl acetate, and the solvent was then removed by distillation. Afterward, the product was separated and purified by column chromatography ($CHCl_3$:MeOH=98:2), followed by drying under a reduced pressure. In consequence, 73.2 mg of crystals were obtained, and a yield was 89%.

Example 2

Synthesis of 2-benzoyl-6,7-difluoro-3-phenylquinoxaline 1,4-dioxide 5,6-difluorobenzofuroxan (34.4 mg, 0.2 mmol) and dibenzoylmethane (47.1 mg, 1.05 eqs) were dissolved in 8 mL of dichloromethane, and 6 g of silica gel (wakogel C-200) was then added thereto, followed by evaporating a solvent, to adsorb them on the silica gel. Afterward, the solvent was completely removed with a vacuum pump, and the material was irradiated with microwaves (700 W) for two minutes. The resultant reaction product was extracted with ethyl acetate, and the solvent was then removed by distillation. Afterward, the product was separated and purified by column chromatography (n-hexane:EtOAc=3:2), followed by drying under a reduced pressure. In consequence, 68.4 mg of crystals were obtained, and a yield was 90%.

A compound synthesized in this manner was analyzed with NMR or the like to confirm a chemical structure. Results are as follows.

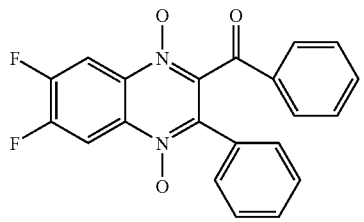

Yellow needle-like crystals, mp. 249 to 251° C. (CHCl$_3$/hexane); IR (KBr) cm$^{-1}$: ν1685, 1503, 1341; $^1$H-NMR (CDCl$_3$): δ7.35-7.47 (m, 7H, H-3', 5', 2", 3", 4", 5", 6"), 7.61 (tt, 1H, J=1.4, 7.6 Hz, H-4'), 7.77 (dd, 2H, J=1.4, 8.3 Hz, H-2', 6'), 8.43 (dd, 1H, J=7.2, 9.3 Hz, H-5), 8.53 (dd, 1H, J=7.2, 9.6 Hz, H-8); $^{13}$C-NMR (CDCl$_3$): δ 108.7 (d, J=23.1 Hz, CH), 109.3 (d, J=23.1 Hz, CH), 126.4 (C), 128.8 (2×CH), 129.0 (2×CH), 129.2 (2×CH), 129.9 (2×CH), 130.9 (CH), 134.6 (C), 134.7 (C), 135.0 (CH), 135.8 (C), 140.0 (C), 141.1 (C), 153.0 (dd, 15.9, 57.8 Hz, C), 154.8 (dd, 15.9, 57.8 Hz, C), 185.3 (C); HRMS (EI) m/z: 378.0816. Calcd. For C$_{21}$H$_{12}$N$_2$O$_3$F$_2$:M, 378.0816.

Example 3

Synthesis of 2-benzoyl-6,7-dimethoxy-3-phenylquinoxaline 1,4-dioxide 5,6-dimethoxybenzofuroxan (39.2 mg, 0.2 mmol) and dibenzoylmethane (47.1 mg, 1.05 eqs) were dissolved in 8 mL of dichloromethane, and 6 g of silica gel (wakogel C-200) was then added thereto, followed by evaporating a solvent, to adsorb them on the silica gel. Afterward, the solvent was completely removed with a vacuum pump, and the material was irradiated with microwaves (700 W) for two minutes. The resultant reaction product was extracted with ethyl acetate, and the solvent was then removed by distillation. Afterward, the product was separated and purified by column chromatography (CHCl$_3$:MeOH=98:2), followed by drying under a reduced pressure. In consequence, 49.8 mg of crystals were obtained, and a yield was 62%.

A compound synthesized in this manner was analyzed with NMR or the like to confirm a chemical structure. Results are as follows.

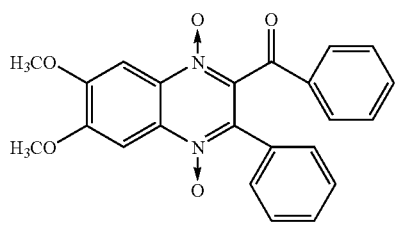

Yellow needle-like crystals, mp. 286° C. dec. (CHCl$_3$/hexane); IR (KBr) cm$^{-1}$: ν1673, 1612, 1502, 1333; $^1$H-NMR (CDCl$_3$): δ4.10 (s, 3H, OCH$_3$), 4.13 (s, 3H, OCH$_3$), 7.34-7.40 (m, 3H, H-3", 4", 5"), 7.43-7.46 (m, 4H, H-3', 5', 2", 6"), 7.59 (dt, 1H, J=1.4, 7.6 Hz, H-4'), 7.77-7.79 (dd, 2H, J=1.4, 7.6 Hz, H-2', 6'), 7.91 (s, 1H, H-5), 8.01 (s, 1H, H-8); $^{13}$C-NMR (CDCl$_3$) δ 57.0 (CH$_3$), 57.1 (CH$_3$), 98.8 (CH), 99.3 (CH), 127.2 (C), 128.6 (2×CH), 129.0 (2×CH), 129.1 (2×CH), 130.1 (2×CH), 130.4 (CH), 133.3 (C), 134.4 (C), 134.5 (CH), 135.1 (C), 137.9 (C), 139.2 (C), 154.5 (C), 154.9 (C), 186.0 (C); HRMS (EI) m/z: 402.1212. Calcd. For C$_{23}$H$_{18}$N$_2$O$_5$:M, 402.1215.

Example 4

Synthesis of 2-acetyl-6,7-difluoro-3-methylquinoxaline 1,4-dioxide 5,6-difluorobenzofuroxan (34.4 mg, 0.2 mmol) and acetylacetone (21.0 mg, 1.05 eqs) were dissolved in 8 mL of dichloromethane, and 6 g of silica gel (wakogel C-200) was then added thereto, followed by evaporating a solvent, to adsorb them on the silica gel. Afterward, the solvent was completely removed with a vacuum pump, and the material was irradiated with microwaves (700 W) for two minutes. The resultant reaction product was extracted with ethyl acetate, and the solvent was then removed by distillation. Afterward, the product was separated and purified by column chromatography (n-hexane:EtOAc=1:1), followed by drying under a reduced pressure. In consequence, 39.1 mg of crystals were obtained, and a yield was 77%.

A compound synthesized in this manner was analyzed with NMR or the like to confirm a chemical structure. Results are as follows.

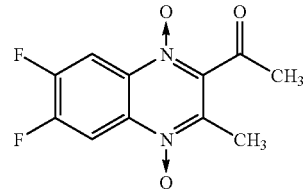

Yellow needle-like crystals, mp. 199 to 200° C. (CHCl$_3$/hexane); IR (KBr) cm$^{-1}$: ν1713, 1517, 1332; $^1$H-NMR (CDCl$_3$): δ2.53 (s, 3H, CH$_3$), 2.73 (s, 3H, COCH$_3$), 8.35-8.38 (dd, 1H, J=7.2, 9.3 Hz, H-5), 8.43-8.45 (dd, 1H, J=7.2, 9.3 Hz, H-8); $^{13}$C-NMR (CDCl$_3$): δ13.8 (CH$_3$), 29.8 (CH$_3$), 108.4 (d, J=23.1 Hz, CH), 108.6 (d, J=23.1 Hz, CH), 133.8 (d, J=8.7 Hz, C), 135.0 (d, J=8.7 Hz, C), 139.7 (C), 140.0 (C), 152.5 (dd, J=15.9, 98.3 Hz, C), 154.5 (dd, 15.9, 98.3 Hz, C), 193.6 (C); HRMS (EI) m/z: 254.0502. Calcd. For C$_{11}$H$_8$N$_2$O$_3$F$_2$:M, 254.0503.

Example 5

Synthesis of 2-acetyl-6,7-dimethoxy-3-methylquinoxaline 1,4-dioxide 5,6-dimethoxybenzofuroxan (39.2 mg, 0.2 mmol) and acetylacetone (21.0 mg, 1.05 eqs) were dissolved in 8 mL of dichloromethane, and 6 g of silica gel (wakogel C-200) was then added thereto, followed by evaporating a solvent, to adsorb them on the silica gel. Afterward, the solvent was completely removed with a vacuum pump, and the material was irradiated with microwaves (700 W) for two minutes. The resultant reaction product was extracted with ethyl acetate, and the solvent was then removed by distillation. Afterward, the product was separated and purified by column chromatography (n-hexane:EtOAc 1:1), followed by drying under a reduced pressure. In consequence, 33.5 mg of crystals were obtained, and a yield was 60%.

A compound synthesized in this manner was analyzed with NMR or the like to confirm a chemical structure. Results are as follows.

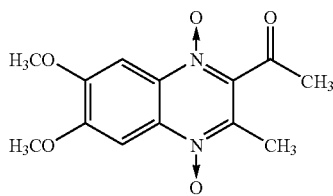

Yellow needle-like crystals, mp. 254° C. (CHCl$_3$/hexane); IR (KBr) cm$^{-1}$: ν1717, 1609, 1498, 1329;
$^1$H-NMR (CDCl$_3$): δ2.54 (s, 3H, CH$_3$), 2.74 (s, 3H, COCH$_3$), 4.09 (s, 3H, OCH$_3$), 4.11 (s, 3H, OCH$_3$), 7.83 (s, 1H, H-5), 7.92 (s, 1H, H-8); $^{13}$C-NMR (CDCl$_3$): δ13.7 (CH$_3$), 30.1 (CH$_3$), 56.9 (CH$_3$), 57.0 (CH$_3$), 98.3 (CH), 98.7 (CH), 132.4 (C), 133.9 (C), 137.6 (C), 138.4 (C), 154.0 (C), 154.8 (C), 194.4 (C);
HRMS (EI) m/z: 278.0902. Calcd. For C$_{13}$H$_{14}$N$_2$O$_5$:M, 278.0902.

Example 6

Synthesis of 6,7-dichloro-3-methyl-2-(4'-nitrobenzoyl)-quinoxaline 1,4-dioxide 5,6-dichlorobenzofuroxan (41 mg, 0.2 mmol) and 4-nitrobenzoylacetone (43.5 mg, 1.05 eqs) were dissolved in 8 mL of dichloromethane, and 6 g of silica gel (wakogel C-200) was then added thereto, followed by evaporating a solvent, to adsorb them on the silica gel. Afterward, the solvent was completely removed with a vacuum pump, and the material was irradiated with microwaves (700 W) for two minutes. The resultant reaction product was extracted with ethyl acetate, and the solvent was then removed by distillation. Afterward, the product was separated and purified by column chromatography (n-hexane:EtOAc=3:2), followed by drying under a reduced pressure. In consequence, 46 mg of crystals were obtained, and a yield was 58%.

A compound synthesized in this manner was analyzed with NMR or the like to confirm a chemical structure. Results are as follows.

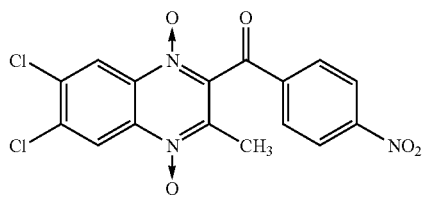

Yellow needle-like crystals, mp. 215 to 217° C. (CHCl$_3$/hexane); IR (KBr) cm$^{-1}$: ν3427, 1692, 1325; $^1$H-NMR (CDCl$_3$): δ2.51 (s, 3H, 3-CH$_3$), 8.04 (d, 2H, J=8.9 Hz, H3', 5'), 8.36 (d, 2H, J=8.9 Hz, H2', 6'), 8.63 (s, 1H, H5), 8.80 (s, 1H, H8); $^{13}$C-NMR (CDCl$_3$): δ14.2 (CH$_3$), 121.6 (CH), 121.9 (CH), 124.6 (2×CH), 130.0 (2×CH), 135.4 (C), 136.8 (C), 138.0 (C), 138.2 (C), 138.5 (C), 139.2 (C), 140.8 (C), 151.4 (C), 185.0 (C); HRMS (EI) m/z: 392.9913 (M$^+$). Calcd. for C$_{16}$H$_9$N$_3$O$_5$Cl$_2$:M, 392.9919.

Example 7

Synthesis of 6,7-difluoro-3-methyl-2-(41-nitrobenzoyl)-quinoxaline 1,4-dioxide 5,6-difluorobenzofuroxan (34.4 mg, 0.2 mmol) and 4-nitrobenzoylacetone (43.5 mg, 1.05 eqs) were dissolved in 8 mL of dichloromethane, and 6 g of silica gel (wakogel C-200) was then added thereto, followed by evaporating a solvent, to adsorb them on the silica gel. Afterward, the solvent was completely removed with a vacuum pump, and the material was irradiated with microwaves (700 W) for two minutes. The resultant reaction product was extracted with ethyl acetate, and the solvent was then removed by distillation. Afterward, the product was separated and purified by column chromatography (n-hexane:EtOAc=3:2), followed by drying under a reduced pressure. In consequence, 26.3 mg of crystals were obtained, and a yield was 36%.

A compound synthesized in this manner was analyzed with NMR or the like to confirm a chemical structure. Results are as follows.

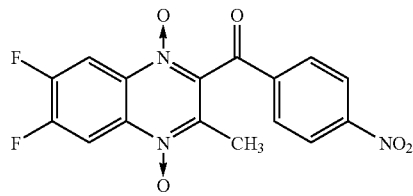

Yellow needle-like crystals, mp. 232 to 233° C. (CHCl$_3$/hexane); IR (KBr) cm$^1$: ν3065, 1703, 1528, 1333; $^1$H-NMR (DMSO-d$_6$): δ2.52 (s, 3H, 3-CH$_3$), 8.05 (dt, 2H, J=2.1, 8.9 Hz, H3', 5'), 8.33 (dd, 1H, J=7.2, 9.3 Hz, H5), 8; 38(dt, 2H, J=2.1, 8.9 Hz, H2', 6'), 8.51 (dd, 1H, J=7.2, 9.6 Hz, H8); HRMS (EI) m/z: 361.0509 (M$^+$). Calcd. for C$_{16}$H$_{11}$N$_3$O$_5$F$_2$: M, 362.0510.

(Hypoxic Selective Cytotoxicity Test with Respect to HepG2 Cells)

A cytotoxicity reinforcing effect on a hypoxic condition was tested using HepG2 cells which were human liver cancer cells. In a usual oxygen state (noroxia) and a hypoxic state (hypoxia), 20 μM of each quinoxaline 1,4-dioxide derivative shown in Table 1 (Compounds 1 to 8 including R$_1$ to R$_6$ shown in Table 1 in the above general formula (3)) was exposed for six hours, and cultivated for seven days, and then colony forming ratios were compared. It is to be noted that in Table 1, "Ph-NO$_2$" is a group in which a nitro group is introduced into a para position of a benzoyl group.

TABLE 1

| | $R_1$ | $R_2$ | $R_3$ | $R_4$ | $R_5$ | $R_6$ | Activity (Surviving fraction) (%) | |
|---|---|---|---|---|---|---|---|---|
| | | | | | | | noroxia | hypoxia |
| Compound 1 | H | H | H | H | $CH_3$ | Ph | 92 | 98 |
| Compound 2 | H | Cl | Cl | H | $CH_3$ | Ph | 53 | 10 |
| Compound 3 | H | F | F | H | $CH_3$ | Ph | 93 | 71 |
| Compound 4 | H | $CH_3$ | $CH_3$ | H | $CH_3$ | Ph | 92 | 112 |
| Compound 5 | H | $OCH_3$ | $OCH_3$ | H | $CH_3$ | Ph | 97 | 110 |
| Compound 6 | H | H | H | H | $CH_3$ | Ph—$NO_2$ | 98 | 28 |
| Compound 7 | H | Cl | Cl | H | $CH_3$ | Ph—$NO_2$ | 73 | 6 |
| Compound 8 | H | F | F | H | $CH_3$ | Ph—$NO_2$ | 44 | 1 |

As shown in Table 1, hypoxic selectivity is obtained in a compound having electron-attracting substituents, especially chlorine atoms in positions 6 and 7 of a quinoxaline skeleton. Moreover, activity is remarkably improved with respect to the hypoxic cells in a compound in which the nitro group is introduced into the para position of the second benzoyl group of the quinoxaline skeleton.

INDUSTRIAL APPLICABILITY

In a method of synthesizing a quinoxaline derivative according to the present invention, a base is not used as a catalyst, and a solid support is used, so that there is provided a method of synthesizing a quinoxaline derivative in which toxicity, corrosiveness and permeation are low and which is excellent in safety and which attains a reduced reaction time, a greatly improved yield and excellent economical efficiency, and there is further provided a novel quinoxaline 1,4-dioxide derivative.

The invention claimed is:

1. A quinoxaline 1,4-dioxide which is represented by the following formula (4):

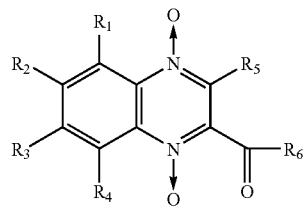

(4)

in which
$R_1$ is hydrogen,
$R_2$ and $R_3$ are each independently a halogen atom or a methoxy group,
$R_4$ is hydrogen,
$R_5$ is a $C_1$ to $C_4$ alkyl group, and
$R_6$ is the following:

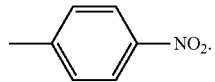

* * * * *